United States Patent
Glatzer et al.

(10) Patent No.: US 8,858,605 B1
(45) Date of Patent: Oct. 14, 2014

(54) TAB BONE SCREW SYSTEM

(71) Applicant: Amendia, Inc., Marietta, GA (US)

(72) Inventors: Michael Glatzer, Alpharetta, GA (US); Challis King, Florence, SC (US); Wells Yang, Johns Creek, GA (US); Dale Whipple, Acworth, GA (US); Bruce Hooper, Waleska, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/199,573

(22) Filed: Mar. 6, 2014

(51) Int. Cl.
*A61B 17/86* (2006.01)
*A61B 17/70* (2006.01)

(52) U.S. Cl.
CPC .......... *A61B 17/7001* (2013.01); *A61B 17/8685* (2013.01)
USPC ........... 606/307; 606/305; 606/306; 606/308; 606/266; 606/267

(58) Field of Classification Search
CPC ........... A61B 17/7032; A61B 17/7034; A61B 17/7035; A61B 17/844; A61B 17/8605; A61B 17/86; A61B 17/8685
USPC ........ 606/305–308, 328, 266–267, 270, 86 A
See application file for complete search history.

(56) References Cited

U.S. PATENT DOCUMENTS

| | | | |
|---|---|---|---|
| 7,927,360 B2 | 4/2011 | Pond | |
| 7,967,821 B2 | 6/2011 | Sicvol | |
| 8,262,662 B2 | 9/2012 | Beardsley | |
| 8,376,940 B2 | 2/2013 | Gorek | |
| 8,388,659 B1 * | 3/2013 | Lab et al. | 606/265 |
| 2008/0300638 A1 * | 12/2008 | Beardsley et al. | 606/306 |
| 2010/0036432 A1 * | 2/2010 | Ely | 606/301 |
| 2011/0040335 A1 * | 2/2011 | Stihl et al. | 606/302 |
| 2011/0178560 A1 | 7/2011 | Butler | |
| 2013/0172937 A1 | 7/2013 | Davenport | |

* cited by examiner

*Primary Examiner* — Eduardo C Robert
*Assistant Examiner* — Julianna N Harvey
(74) *Attorney, Agent, or Firm* — David L King

(57) ABSTRACT

Presented herein is a bone screw system that comprises a fixation element, a receiving element, coupling element, and a compression element. The fixation element can be a screw. The receiving element defines an internal bore sized to receive the shank portion of the fixation element and a seat adapted to support the head portion of the fixation element. The seat of the receiving element is shaped to substantially conform to an exterior portion of the head portion of the fixation element. A breakaway groove is positioned externally on each leg or leg extension. The breakaway groove extends inwardly at least partially through the wall of each leg or leg extension. This creates an aperture or slit in the wall leaving the wall with at least on, preferably a pair of leg attachments on each leg or leg extension adjacent the aperture.

24 Claims, 18 Drawing Sheets

TAB BONE SCREW SYSTEM

TECHNICAL FIELD

The present disclosure relates to a bone screw system. More specifically, a bone screw system with an improved tab breakaway feature for use in spinal surgery is presented.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

Those bone screw connectors often employ tabs or towers to facilitate the assembly. Once the screws and rods are fixed in place, these tabs or towers are removed from the connector. Various means to remove the tabs have been used including releasable pins and frangible tear or fracture seams. The tabs or towers often called extension legs vary in length from short, an inch or less, to very long, four or more inches. The removal of these extension legs needs to be simple and reliable. Most preferably, the removal needs to be consistent. The attachment must be secure so as not to prematurely fail, but not so strong as to require large forces or multiple flexing to release the legs. Some prior art bone screws have resorted to separate tools to initiate a breakage of a connection due in part to the excessive forces required, as taught in U.S. Pat. No. 7,927,360.

It is an object of the present invention to provide an easier to use, more reliable breakaway feature.

SUMMARY OF THE INVENTION

Presented herein is a bone screw system that comprises a fixation element, a receiving element, coupling element, and a compression element. The fixation element can be a screw. The receiving element defines an internal bore sized to receive the shank portion of the fixation element and a seat adapted to support the head portion of the fixation element. The seat of the receiving element is shaped to substantially conform to an exterior portion of the head portion of the fixation element.

The receiving element is further adapted to receive a stabilizer rod. As such, in one aspect, the receiving element comprises a pair of opposed legs separated by a rod-receiving channel. In another aspect, the bone screw system also comprises a pair of leg extensions. Each leg extension has a first end and a second end, where the second end is coupled to a respective opposed leg of the receiving element.

The compression element is engagable with the receiving element. In one aspect, the compression element is adapted to move downward into the compression element receiving chamber to translate a force to the stabilizer rod and translate a force onto the head portion of the fixation element and substantially fix the position of the fixation element with respect to the receiving element.

In one embodiment, a breakaway groove is positioned externally on each leg or leg extension. The breakaway groove extends inwardly at least partially through the wall of each leg or leg extension. This creates an aperture or slit in the wall leaving the wall with at least one, preferably a pair of leg attachments connecting each leg to each respective leg extension adjacent the aperture.

In a preferred embodiment, the leg extensions also have threads continuing from the legs along its length at distances equal or less than the length of the leg extension. The threads accept the external threads of the compression element. The wall thickness of the legs or leg extension is a minimum (t) at the thread groove and the breakaway groove extends to at least a portion of a thread groove at the distance of (t) or greater. The internal threads of the legs and leg extensions have a pitch so the threads form a helix angle and the breakaway groove intersects the pitch along at least one thread or thread groove.

The breakaway groove is oriented perpendicular to an axis of the receiving channel. In a preferred embodiment, the breakaway groove can employ a second cut at a leading or trailing end or preferably both in the form of an undercut to create an enlarged opening. The undercut can be any shape, round, square or angled and this feature due to the arcuate shape of the legs is the point of fracture break initiation. The undercut directs to break along the breakaway groove and also can shorten the amount of leg attachment to facilitate breakage.

When formed, the breakaway groove has a straight upper groove wall on a side on or next to the leg extensions and a lower groove wall that is straight with a chamfered outer portion.

Ideally, the leg attachments of the breakaway groove breaks when the leg extension is bent at 20 degrees or less, preferably 10 degrees, of a bend angle and less than 10 pounds, but greater than 2 pounds, preferably between 3 and 7 pounds. The leg attachments extend a combined distance of 75% or less of the arcuate width of each of the legs or leg extensions to which they are coupled. The breakaway groove can be positioned entirely in the opposed legs, or entirely in the leg extensions or where the legs and leg extensions are coupled. The receiving element with legs and leg extensions are preferably made of implantable metal such as stainless steel or preferably titanium or a titanium alloy.

Other aspects and embodiments of the bone screw system are described herein. This description is meant to fully describe the bone screw system, but not limit its design, function, or application.

BRIEF DESCRIPTION OF THE DRAWINGS

The invention will be described by way of example and with reference to the accompanying drawings in which.

DETAILED DESCRIPTION OF THE INVENTION

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention relates to an improvement over co-pending patent application Ser. No. 13/720,525 now published US 2013/0172937 A1 filed Dec. 19, 2012 which is incorporated by reference herein in its entirety.

Figure 1:
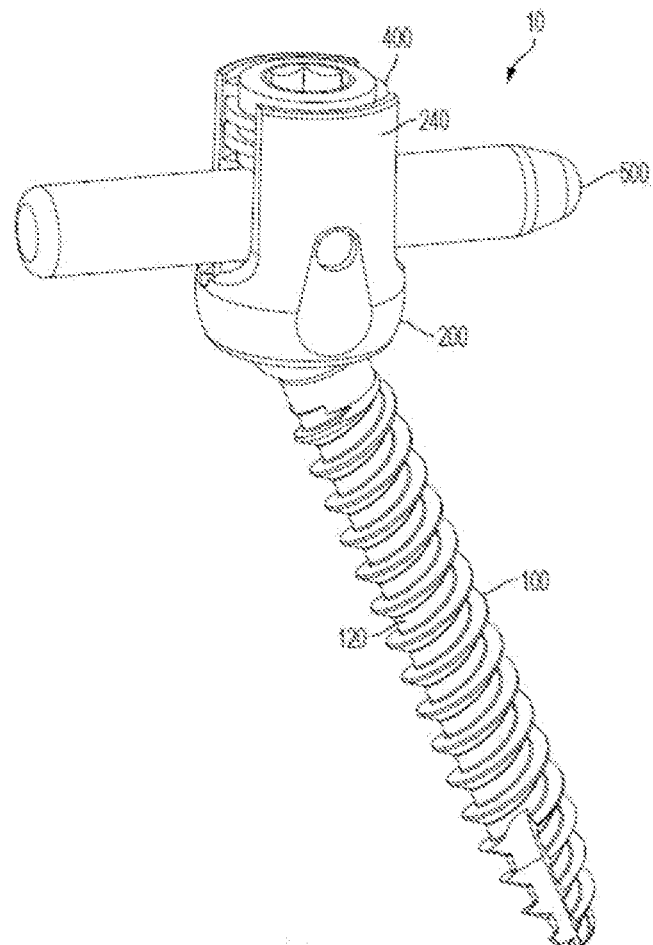
FIG. 1 is a perspective view of one aspect of a bone screw system.
Figure 2:
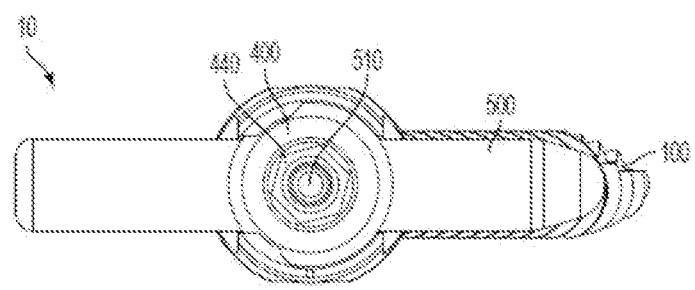
FIG. 2 is a top plan view of the bone screw system of FIG. 1, showing a portion of the stabilizer rod.
Figure 4:
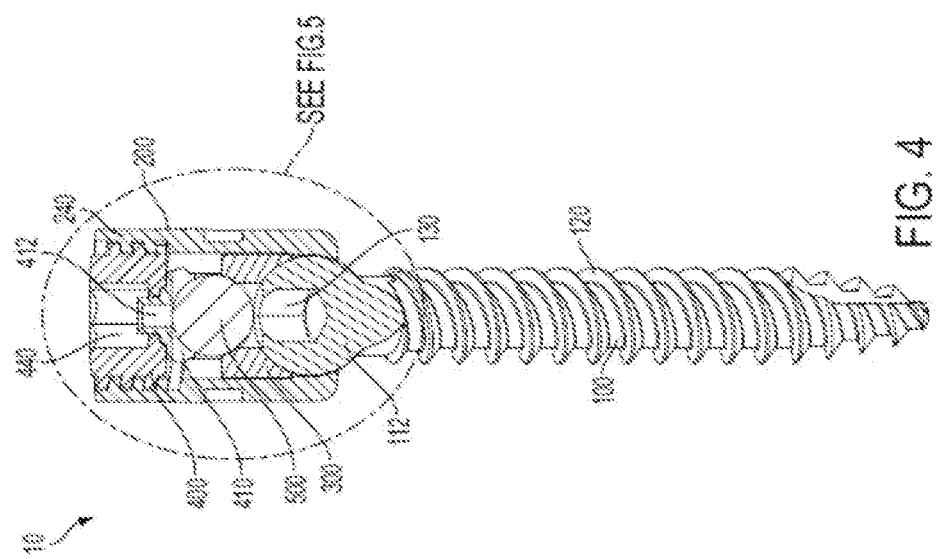
FIG. 4 is a cut-away right side elevation view of the bone screw system of FIG. 1, cut along line 4-4 of FIG. 3.
Figure 3:
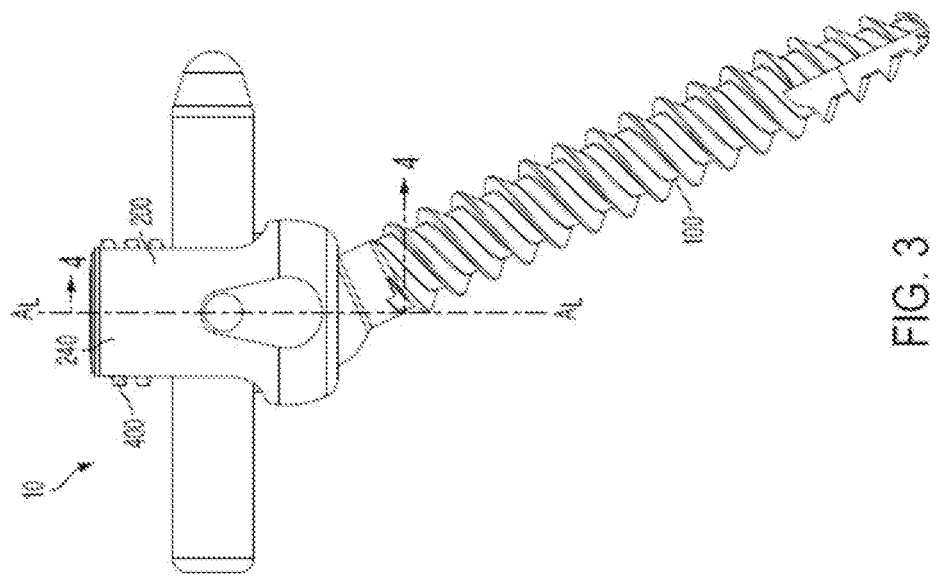
FIG. 3 is a front elevational view of the bone screw system of FIG. 1.
Figure 5:
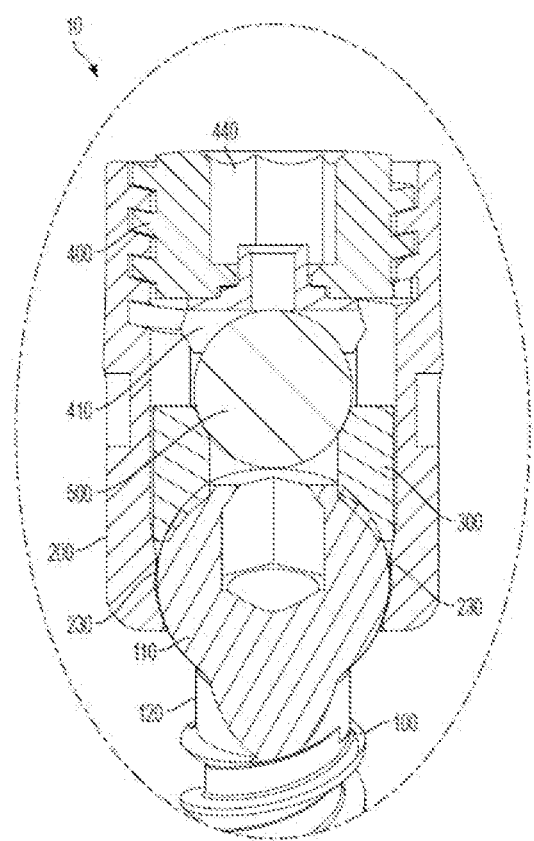
FIG. 5 is an exploded cut-away front elevational view of Section 5 of FIG. 4 of the bone screw system of FIG. 1
Figures 6, 7:
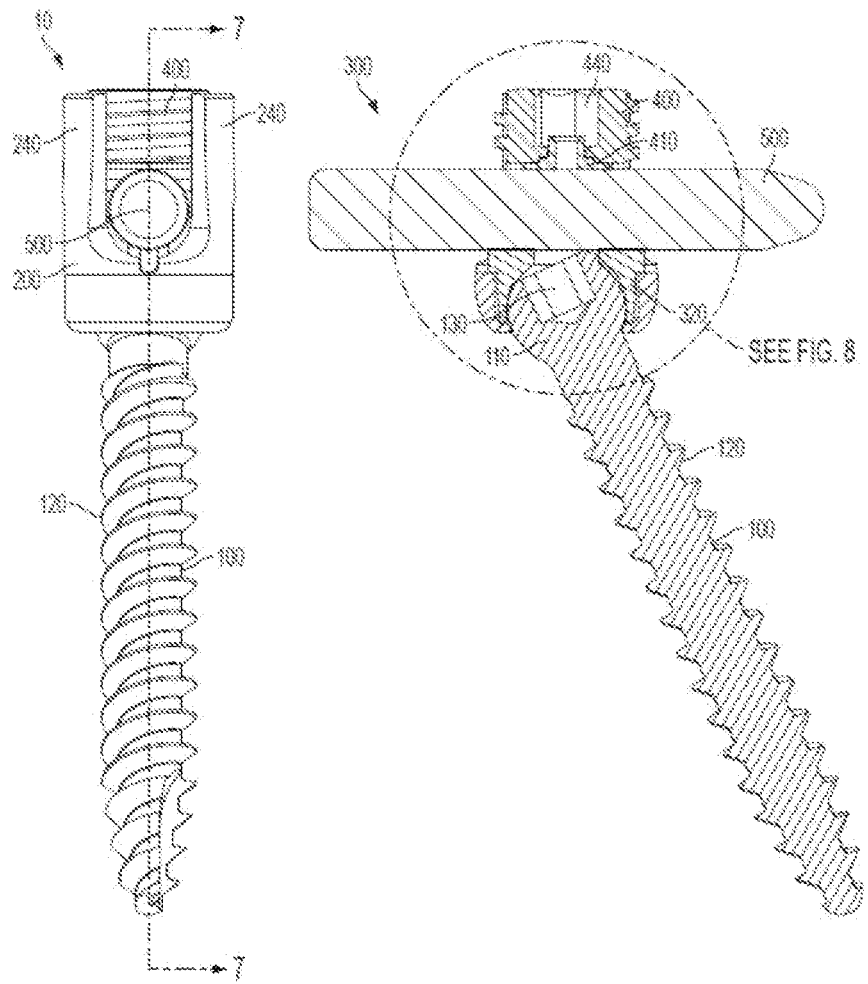
FIG. 6 is a right side elevational view of the bone screw system of FIG. 1.
FIG. 7 a cut-away front elevational view of the bone screw system of FIG. 1, cut along line 7-7 of FIG. 6.
Figure 8:
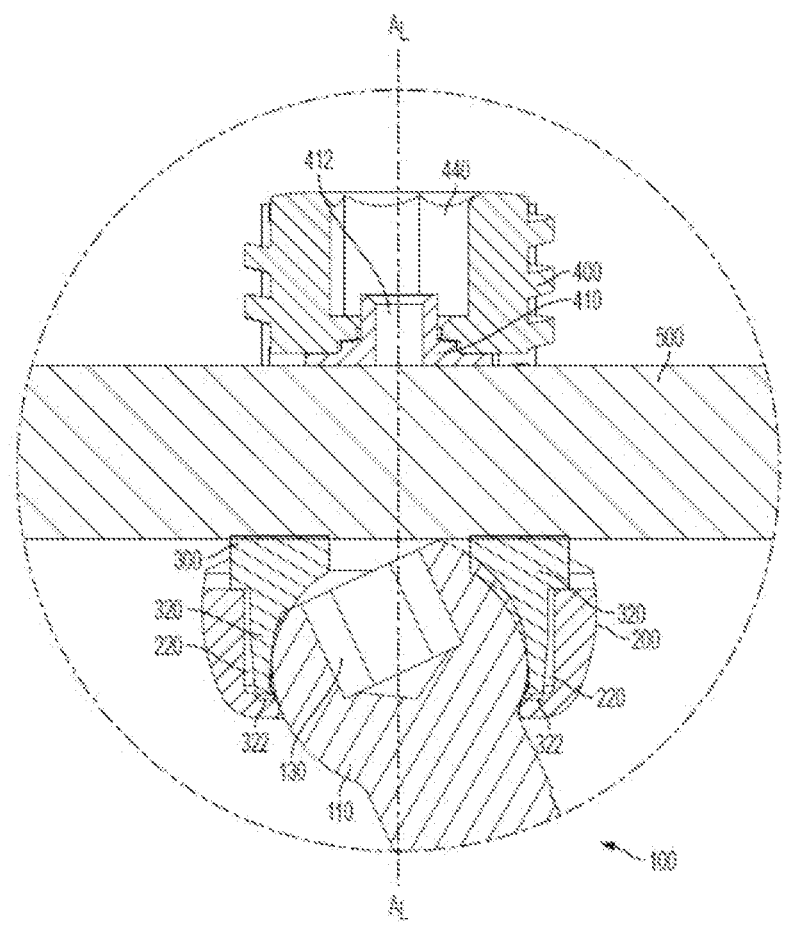
FIG. 8 is an exploded cut-away front elevational view of Section 8 of FIG. 7 of the bone screw system of FIG. 1.
Figure 9:
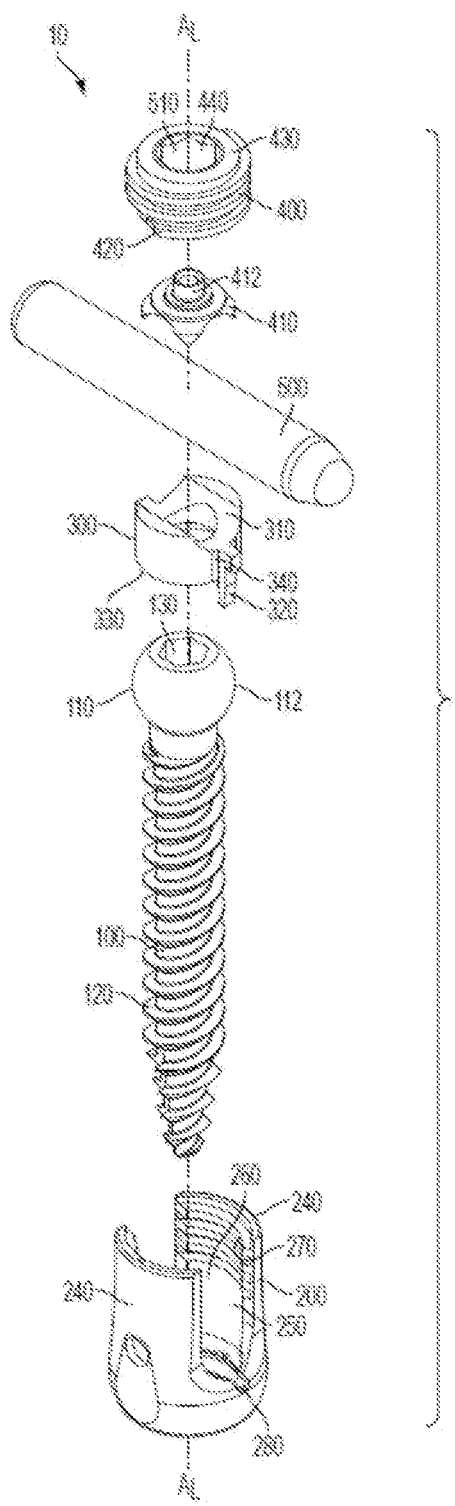
FIG. 9 is an exploded front perspective view of the bone screw system of FIG. 1.

Presented herein is a bone screw system 10 that comprises a fixation element 100, a receiving element 200, coupling element 300, and a compression element 400, as shown in FIGS. 1 and 4. In one aspect, the fixation element 100 is adapted to engage a bone and has a head portion 110 and a threaded shank portion 120, as shown in FIGS. 1 through 13. The fixation element can be a screw. In an exemplified aspect, the head portion 110 is substantially spherical, or substantially semispherical, although other shapes are contemplated. As one skilled in the art can appreciate, the fixation element 100 can comprise a pedicle screw, such as a standard fast-pitch, double-lead pedicle screw. As such, the head portion 110 can be configured to engage the particular insertion tool designed for the system 10. In one aspect, the head portion of the fixation element defines a screw tool bore 130 configured for engagement with the insertion tool. As illustrated in FIG. 9, the screw tool bore 130 can be a hex shaped bore or other shape that mates with a corresponding insertion tool or driver.

Figure 11:
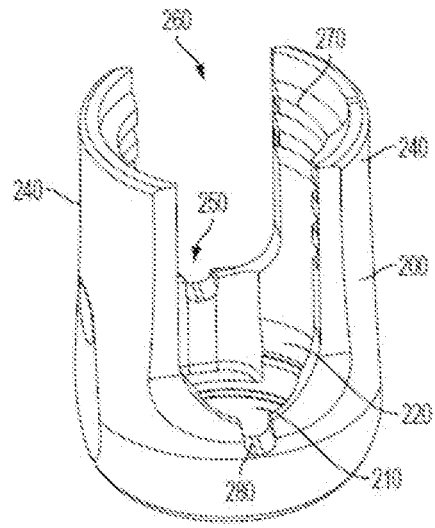
FIG. 11 is a perspective view of one aspect of a receiving element for use in a bone screw system.
Figure 12:
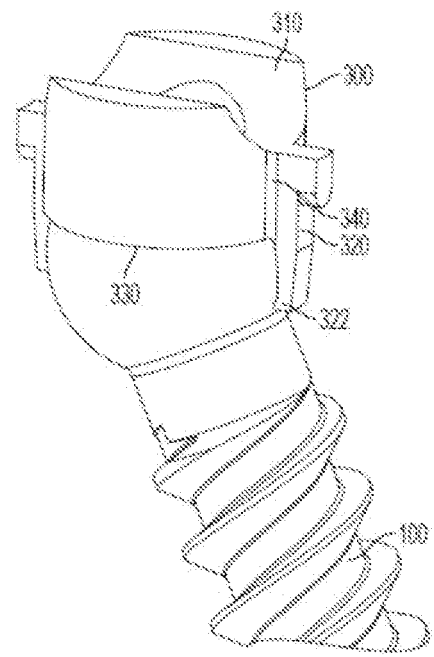
FIG. 12 is a perspective view of one aspect of a coupling element coupled thereto a head portion of a fixation element of for use with a bone screw system.
Figure 13:
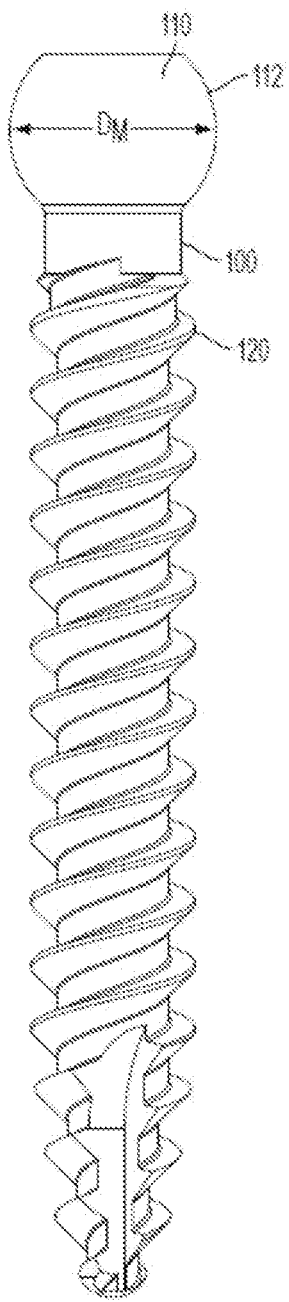
FIG. 13 is a side elevational view of one aspect of a fixation element for use with a bone screw system.

The receiving element 200, as illustrated in FIG. 11, defines an internal bore 210 sized to receive the shank portion 120 of the fixation element 100 and a seat 220 adapted to support the head portion 110 of the fixation element. The seat 220 of the receiving element is shaped to substantially conform to an exterior portion 112 of the head portion 110 of the fixation element 100 as shown in FIGS. 11 and 13. The receiving element 200 can be configured in various ways, as those skilled in the art can appreciate.

The receiving element 200 is further adapted to receive a stabilizer rod 500. As such, in one aspect, the receiving element 200 comprises a pair of opposed legs 240 separated by a rod-receiving channel 250. As illustrated in FIG. 9, the rod receiving channel 250 is sized for complementary engagement with a portion of the stabilizer rod 500. The compression element 400, as discussed below, is configured to work with the receiving element 200 to compress the stabilizer rod 500 onto the coupling element 300, although the system can work without the use of a coupling element. The compression of the stabilizer rod 500 into the receiving element 200 can be accomplished in several manners, including but not limited to, externally threading the two legs 240 for engagement with an internally threaded nut, or internally threading the two legs for engagement with an externally threaded set screw. As such, in this aspect, the pair of opposed legs 240 defines a compression element receiving chamber 260, shown in FIG. 11. In one exemplified aspect, the threads of the opposed legs 240 and complimentary threads of compression element 400 can comprise square threads. As one skilled in the art can appreciate, other thread patterns, such as but not limited to, inwardly tilted threads, dove tail threads, and the like, may be used.

In one exemplified aspect shown in FIG. 8, the coupling element 300 is positioned in the receiving element 200 below the stabilizer rod 500 when the stabilizer rod is in the receiving element. In one aspect, a top portion 310 of the coupling element 300 is substantially saddle-shaped to substantially conform to the shape of the stabilizer rod 500 to maximize contact surface area between the coupling element 300 and the stabilizer rod 500. The coupling element 300 provides additional surface area of contact between the stabilizer rod 500 and the head 110 of the fixation element 100, so when the compression element is in place, the force of the compression element maintains the orientation of the fixation element.

Figure 17:
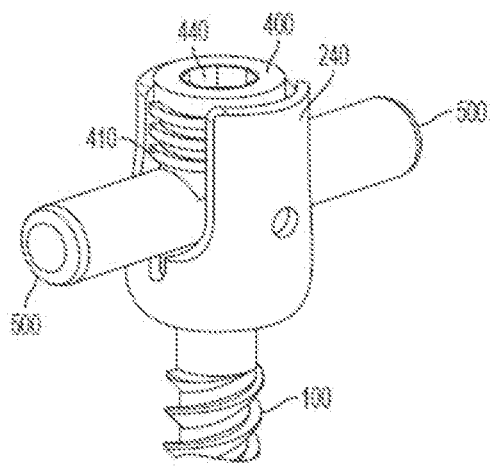
FIG. 17 is a perspective view of a bone screw system, showing a top saddle having a rod trough.

The compression element 400 is engagable with the receiving element 200, as discussed herein. In one aspect, the compression element 400 is adapted to move downward into the compression element receiving chamber 260 to translate a force to the stabilizer rod 500 and place it into contact with the coupling element 300, which translates a force onto the head portion 110 of the fixation element 100 and substantially fixes the position of the fixation element 100 with respect to the receiving element 200. If the system is without a coupling element 300, the stabilizer rod 500 can exert the force onto the head portion 110 of the fixation element 100 directly, shown in FIG. 17.

Figure 10:
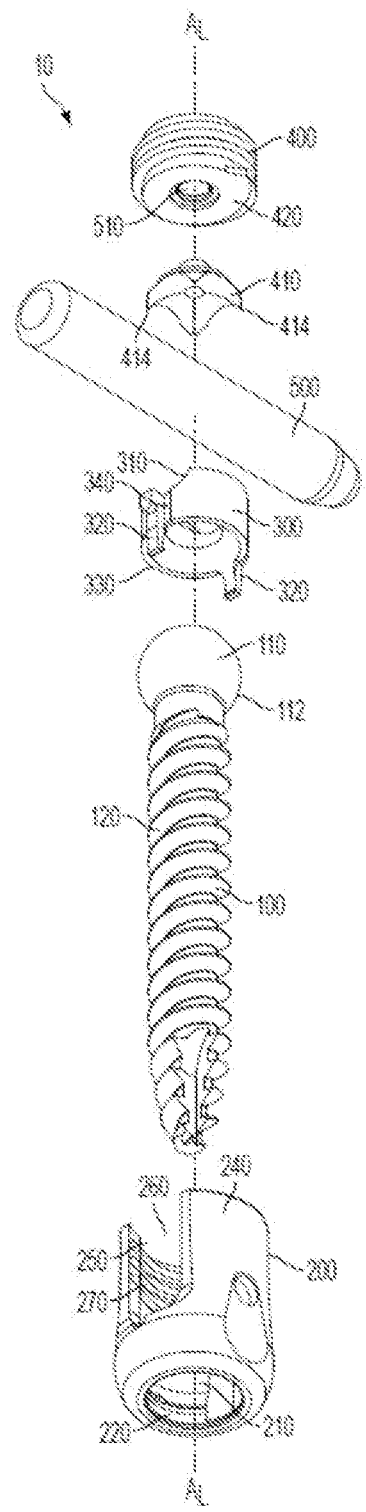
FIG. 10 is an exploded rear perspective view of the bone screw system of FIG. 1.
Figure 18A:
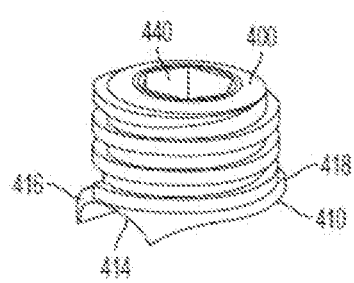
FIG. 18A is a perspective view of a compression element and a top saddle with a rod trough.
Figure 18B:
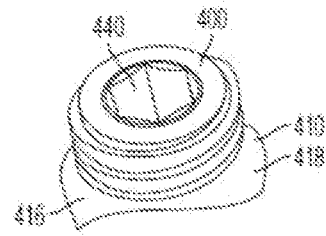
FIG. 18B is a perspective view of the compression element and top saddle of FIG. 18A.

In still another aspect shown in FIGS. 9 and 10, the compression element 400 can further comprise a top saddle 410 rotatingly positioned on its bottom face 420. It can, for example, be mounted to the bottom face 420 of the compression element. Alternately, as illustrated in FIG. 9, the top saddle 410 can comprise a male protrusion 412 designed to penetrate the compression element 400 and be retained thereby. In this aspect, the top saddle self-aligns into secure engagement with the stabilizer rod 500 as the top saddle moves downward toward the stabilizer rod. This design maximizes the contact surface area between the compression element 400 and the stabilizer rod 500. The top saddle 410 shown in FIG. 18A shows a top saddle 410 comprising a rod trough 414 substantially conformable to the surface of the stabilizer rod. In one exemplified aspect, the top saddle comprises a proximal end 416 and a distal end 418, where at least one of the two ends extends out of the compression element receiving chamber substantially along the longitudinal axis $A_R$ of the rod-receiving channel, shown in FIG. 15. In this fashion, the orientation of the top saddle 410 is maintained to keep the rod trough 414 in substantially co-linear relation to the longitudinal axis of the rod-receiving channel 250 and is prevented from rotating with the compression element 400 by the two legs 240 of the receiving element 200. In one aspect, the proximal end 416 extends further than the radius of the compression element receiving chamber 260. In another aspect, the distal end 418 extends further than the radius of the compression element receiving chamber. In yet another aspect, both ends extend further than the radius of the compression element receiving chamber 260.

The compression element 400 is designed to be driven into the compression element receiving chamber. In one aspect, the top face 430 of the compression element defines a set screw tool bore 440 configured for engagement with an insertion tool. The set screw tool bore 440 can be, but is not necessarily, configured to engage the same insertion tool as the screw tool bore discussed above.

Some practitioners may desire to position the bone screw system with the aid of one or more guide wires. In this case, the practitioner can place a guide wire into the desired target location. In this aspect, the system defines a coaxial aperture along the longitudinal axis $A_L$, shown in FIGS. 3 and 8. Therefore, in this aspect, the compression element 400, the coupling element 300, and the fixation element each define a coaxial guide wire aperture 510. Where there is a top saddle present in the system, the top saddle also defines a coaxial guide wire aperture 510.

Figure 14:
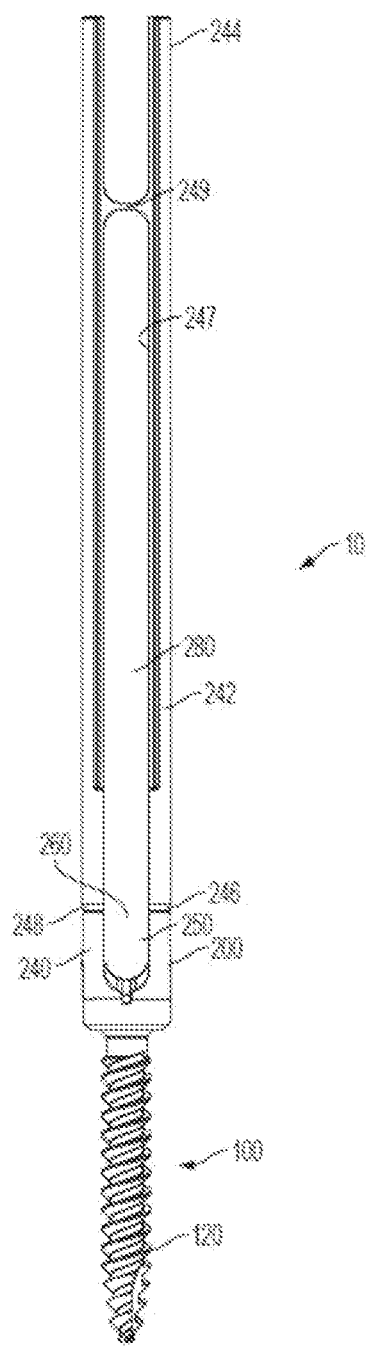
FIG. 14 is a front elevational view of one aspect of a bone screw system, showing a pair of leg extensions and a connector.
Figure 15:
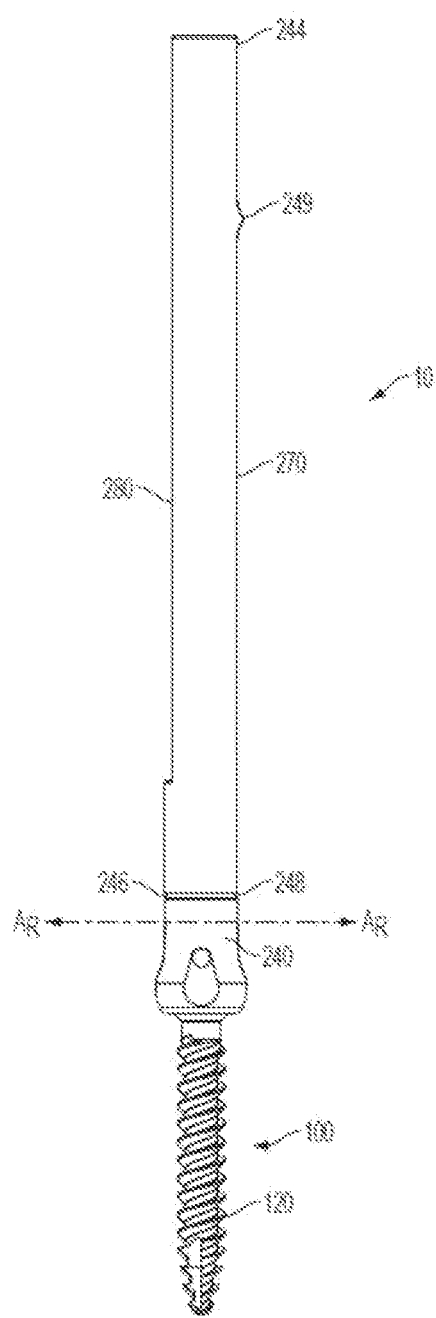
FIG. 15 is a side elevational view of the bone screw system of FIG. 14.
Figure 16:
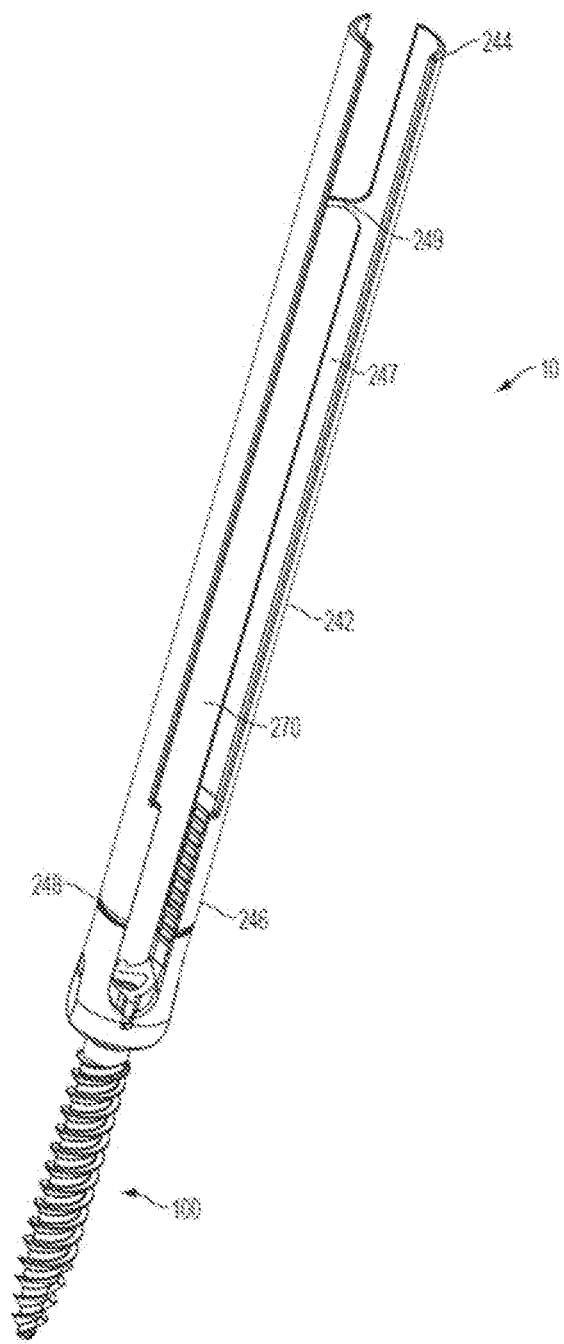
FIG. 16 is a perspective view of the bone screw system of FIG. 14.

In another aspect illustrated in FIGS. 14-16, the bone screw system 10 also comprises a pair of leg extensions 242. Each leg extension has a first end 244 and a second end 246, where the second end 246 is coupled to a respective opposed leg 240 of the receiving element 200. The pair of leg extensions 242 define a first insertion tool pathway 270 therebetween one another and a second insertion tool pathway 280 therebetween one another.

In one aspect, the cross-sectional shape of the leg extensions 242 are substantially similar to the cross-sectional shape of the leg 240 to which it is coupled. As can be appreciated, the cross-sectional dimensions of the leg extensions can also be substantially the same as the cross-sectional dimensions of the legs to which they are coupled, although it is contemplated that the leg extensions can vary in shape and dimension from the legs to which they are coupled. The length of each leg extension 242 can vary, but in any event, the first end 244 of each of the leg extensions 242 extends outside of the patient when the fixation element 100 is positioned within the spine of the patient.

In an exemplified aspect, the two leg extensions 242 are coupled to each respective leg 240 at or near the leg extension's second end 246 in a manner such that the leg extension 242 can be removed from the leg 240 if desired. In one aspect, the leg and the leg extension can be integral, with a reduced thickness portion 248 at or near the point of coupling. In this aspect, sufficient radial pressure exerted near the reduced thickness portion will fracture the reduced thickness portion 248, thereby separating the leg extension from the leg. The reduced thickness portion can be interior, exterior, or both. Interior, in this instance, refers to the side of the leg extension 242 or leg 240 that faces the compression element receiving chamber 260.

The interior face 247 of each of the leg extensions 242 need not be threaded like the legs of the receiving element 200. This configuration permits the compression element 400 to slide between the leg extensions and into the compression element receiving chamber until it reaches the threaded portion. In one aspect shown in FIG. 16, the interior face 247 of the leg extensions is threaded toward the second end 246.

Figure 19:
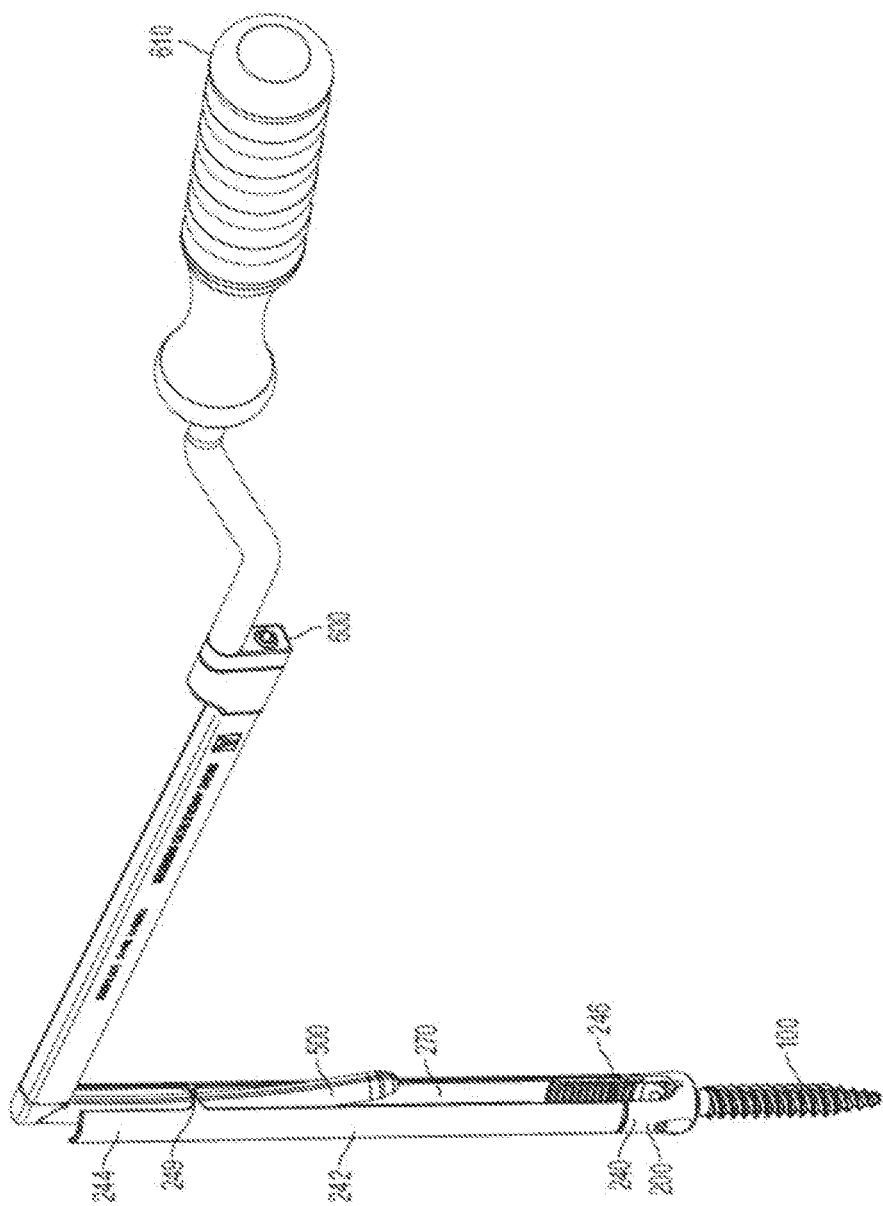
FIG. 19 is a perspective view of an insertion tool, inserting a stabilizer rod into a bone screw system with leg extensions.
Figure 20:
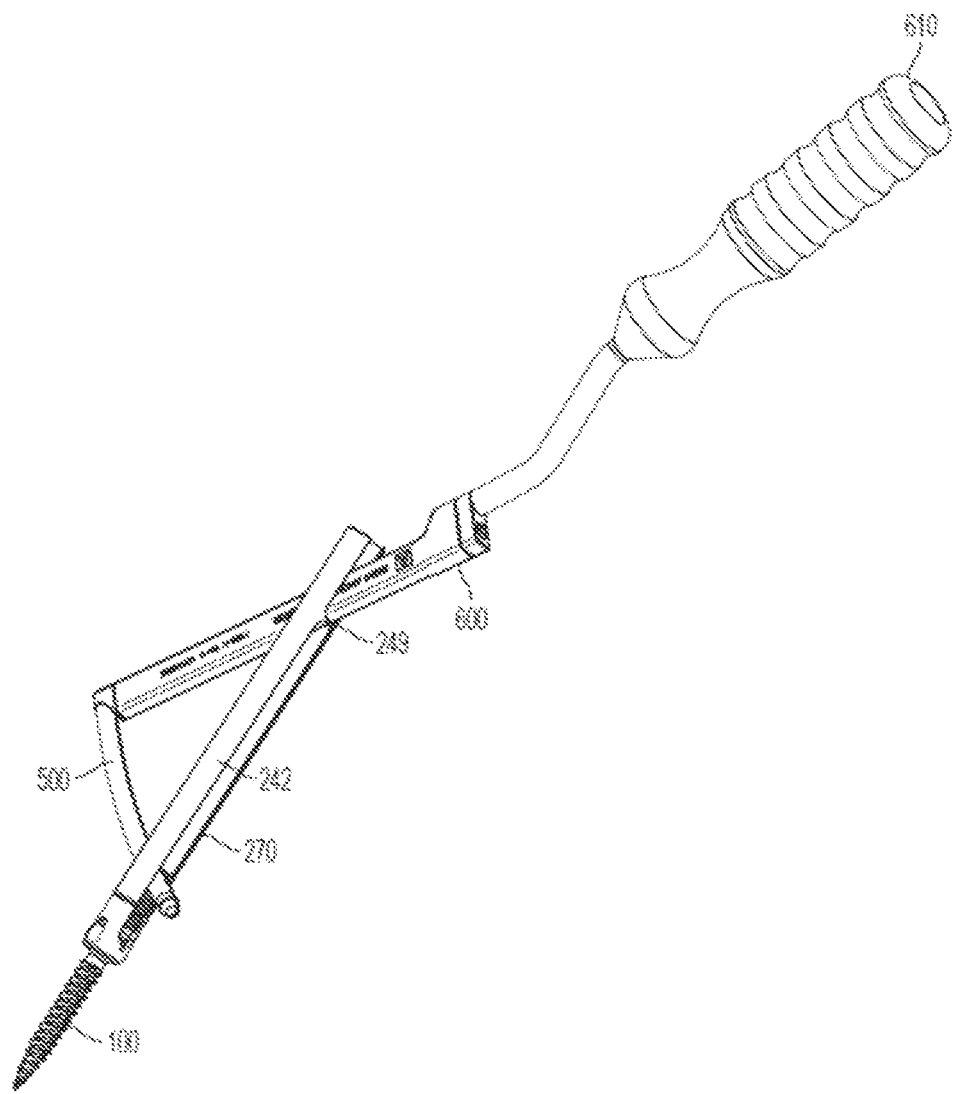
FIG. 20 is a perspective view of the insertion tool of FIG. 19, showing the insertion tool using the connector as a fulcrum to maneuver the stabilizer rod into position.
Figure 21:
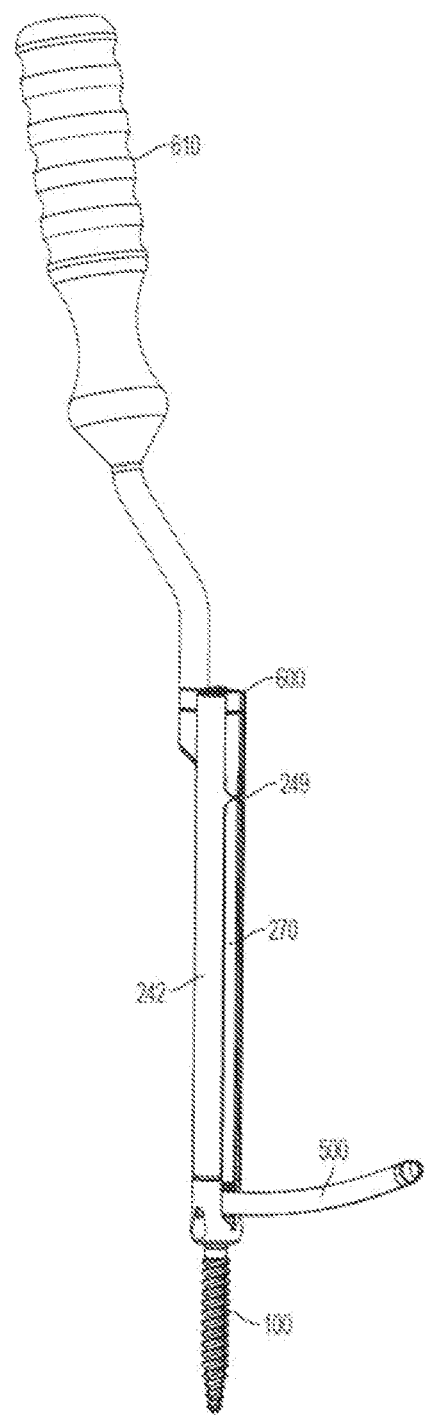
FIG. 21 is a perspective view of the insertion tool of FIG. 19, showing the insertion too using the connector as a fulcrum to further maneuver the stabilizer rod into position.

In another aspect, the two leg extensions 242 are connected via a connector 249 positioned at a point spaced therefrom the first end 244 of the leg extension 242 and spanning the first insertion tool pathway 270. In one aspect, the connector 249 is positioned substantially perpendicular to the longitudinal axis $A_L$. Positioning the connector 249 a predetermined distance from the first end 244 provides a fulcrum point from which a rod insertion tool 600 can rotate. As seen in FIG. 19, the stabilizer rod 500 is positioned between the leg extensions 242 with the insertion tool 600. As the stabilizer rod 500 is positioned lower and toward the second end 246 of the leg extensions, the insertion tool 600 is partially positioned between the leg extensions 242. At this point, the handle 610 of the insertion tool 600 can be lifted, using the connector 249 as a fulcrum to push the stabilizer rod 500 into position within the rod receiving channel 250 as shown in FIGS. 20 and 21.

With reference to FIGS. 22 through 25, an improved breakaway groove 20 has been incorporated into the receiving element 200. The breakaway groove 20 as shown is at a location coupling the legs 240 to the leg extensions 242. This breakaway groove 20 can be positioned anywhere along with the legs 240 or the leg extensions 242 and when the leg extensions 242 are bent off the center axis of the receiving element 200, the breakaway groove 20 at leg attachment locations fractures and breaks allowing that portion of the leg extension or leg above the breakaway groove 20 to be detached and removed from the bone screw assembly 10.

Figure 22:
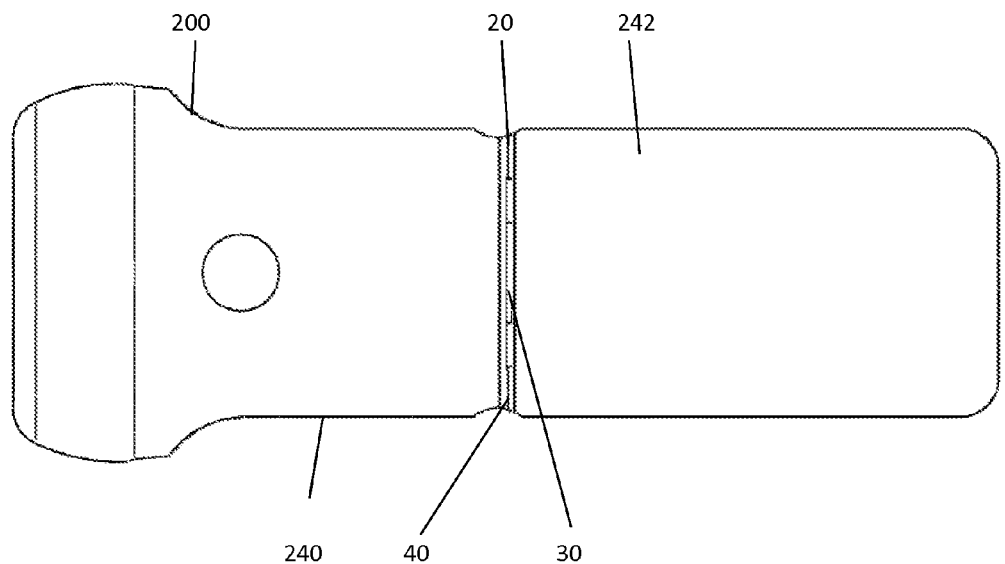
FIG. 22 is a top plan view of the receiving element with opposed legs and coupled leg extensions illustrating the breakaway groove.
Figure 23:
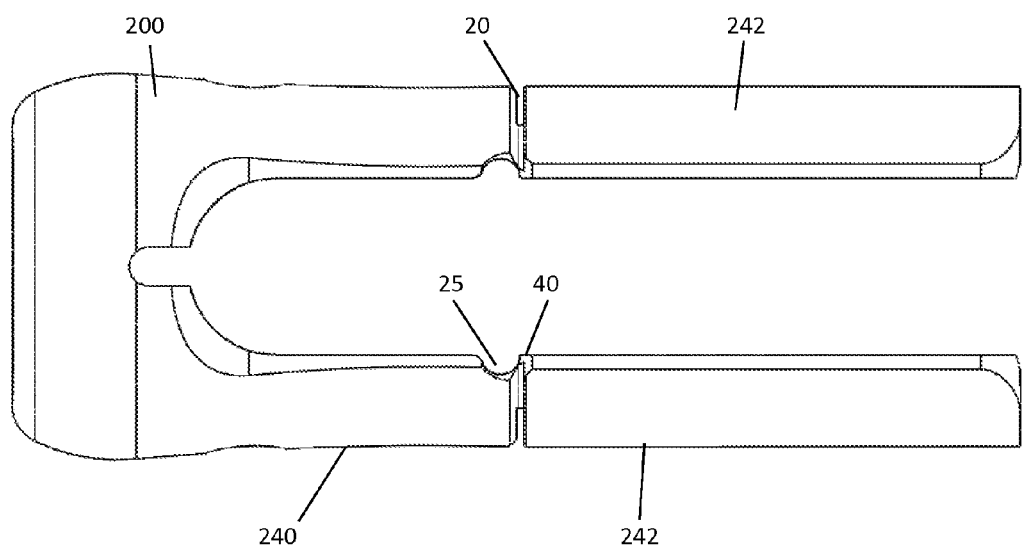
FIG. 23 is a side view of the receiving element with the breakaway groove.

With reference to FIG. 22, as shown, the breakaway groove 20 is cut into the receiving element 200 until it breaks through the wall of the leg 240 or leg extension 242. When this occurs, the cut is so deep it actually creates an aperture or opening slit 30 as shown. On each side of the aperture 30 is a leg attachment 40. The leg attachments 40 are thin breakable features that hold the leg extension 242 to its respective leg 240. As shown in the side view, the receiving element 200 has the breakaway groove 20 on each leg and leg extension held together by the remaining uncut leg attachment 40.

Figure 24:
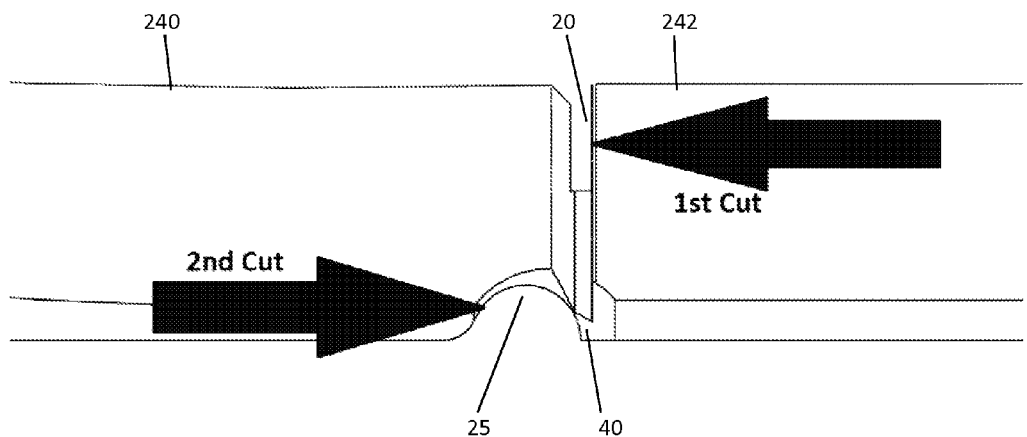
FIG. 24 is an enlarged side view detailing the breakaway groove and the second cuts to direct the break.

The design works by making the break-off section have a tensile failure mode. This first cut 20 from the outside of the receiving element 200 is made until it breaks at least partially through the wall. A specified distance below that cut 20, another cut 25 is made perpendicular to axis of the receiving element 200 to form the half crescent shape opening as shown in FIG. 24. The second cut was made using a round circular drill to create an undercut 25. The undercut while shown round can be any shape such as square, triangular, rectangular, oval or any notched out shape.

As the surgeon pulls the leg extensions 242 away from the central axis of the receiving element 200, the first cut 20 allows the leg extension 242 to push down on itself, replicating a fulcrum. This lever action pulls up on the remaining material, thus causing the tensile failure mode fracturing the leg attachments 40. To limit the angle of bend, it is desirable to make the groove 20 as thin as possible so the fulcrum effect occurs at a low bend angle.

The secondary cut 25 creates a stress riser that directs the location of failure and also modifies the slip plane, thus specifying the location and angle of the created stress riser in such a way that minimizes the size and shape of burrs created by the breaking of the leg attachments 40. To better see this, reference is made to FIG. 24 showing the enlarged opening or undercut created by the second cut 25. As illustrated, the second cut 25 resides slightly below the upper groove wall in the trough of the breakaway groove 20. The second cut 25 removes a portion of the lower chamfered groove wall.

Figure 25:
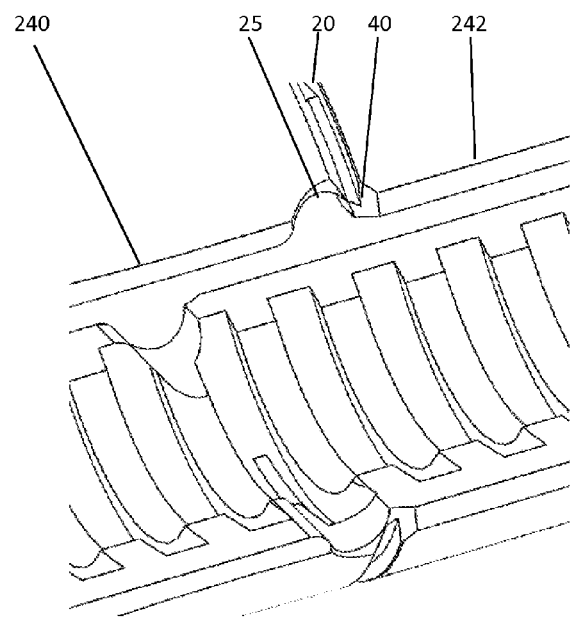
FIG. 25 is a perspective view of the receiving element showing the internal threads and the breakaway groove.

This second cut 25, when viewed in FIG. 25, has removed portions of the remaining leg attachment 40 along each leading and trailing side or edge of the legs 240. This further helps in controlling the amount of bend angle to break and forces required to fracture fail the leg attachments 40. While shown in combination with the breakaway groove 20, it is understood such use of undercuts 25 can be used with any other frangible groove type to reduce the width of a leg attachment joining a leg and leg extension to assist in breakage at lower pound force and reduced angles, and is novel in its use as well.

When using the breakaway groove 20 with the undercuts formed by the second cuts 25 of the present invention, testing illustrated break angles of 6.3 degrees to 11.0 degrees per leg extension. This resulted in the combined break angle being less than 20 degrees between the two leg extensions 242 to achieve breakages. The smaller the angle, the less the extensions need to bend.

Equally importantly, the pounds force needed was between 3 and 7 pounds, typically about 4 to 6 pounds. This means the break angle is sufficiently small to make it relatively easy to deflect the leg extension 242 while the pounds force required means the breakage is high enough to avoid accidental breakage, but low enough to make it easily achieved. It is noted, the longer the leg extension, the more mechanical advantage or leverage is exhibited. The present invention allows the breakaway groove 20 to be used with much shorter leg extensions such as are found on devices called mid top towers that are short, only an inch or so in length.

While the breakaway groove 20, as shown, was formed by cutting a groove, such a groove with its slit or aperture can be pre-machined into the ends of separate legs or leg extensions and joined at these ends by press fitting or welding together the legs to the leg extensions leaving a slit or aperture through the joined leg walls. Such a small aperture can be achieved that is equivalent to a cut, but even thinner. These and other alternative fabrication techniques can be used to create this desired tensile break.

As can be appreciated by one skilled in the art, the materials of construction can vary. The materials of construction are generally biocompatible materials for use in surgery. For example, the bone screw system 10 can comprise Titanium or a Titanium alloy, such as Ti 6-4 ELI. The system can also be bead blasted to increase frictional forces and to add stability to the system.

It must be appreciated that the exemplary bone screw system 10 is just one example of the use of the breakaway groove 20 and the second 25 of the present invention. Other devices having breakaway tabs or towers, but using different designs could use one of either the breakaway groove 20 or second cuts 25 or both to improve a frangible break and such uses of these features singularly or in combination are considered within the scope of the present invention.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone screw system comprising:
   an elongate fixation element adapted to engage a bone and having a head portion and a threaded shank portion;

a receiving element defining an internal bore sized to receive the shank portion of the fixation element and a seat adapted to support the head portion of the fixation element, the receiving element comprising a pair of opposed legs separated by a rod receiving channel sized for complimentary engagement with a stabilizer rod, wherein the pair of opposed legs defines a compression element receiving chamber, each opposed leg having a wall of a thickness with internal threads extending inwardly from each wall;

a pair of leg extensions, one leg extension coupled to each opposed leg;

a compression element configured to engage a portion of the receiving element and be complimentarily received in the compression element receiving chamber, the compression element configured to compress the stabilizer rod into the receiving element to fix the position of the stabilizer rod with respect to the receiving element, the compression element has external threads complimentary to the internal threads of the opposed legs;

a breakaway groove positioned externally between each leg and leg extension, the breakaway groove extending inwardly at least partially through the wall of each leg or leg extension, the breakaway groove extends through the wall between each leg and leg extension to create an aperture, wherein the aperture is positioned leaving the wall having a pair of leg attachments between each leg or leg extension, one leg attachment on each side of the aperture, each leg extension being an arcuate shape; and wherein the leg or leg extension has a second cut at a leading end of the breakaway groove, the second cut being an undercut to create an enlarged opening and another second cut is positioned at the trailing end of the breakaway groove to create an enlarged opening, the second cuts forming a point of fracture break initiation due to the arcuate shape of the legs.

2. The bone screw system of claim 1 wherein the receiving element having the internal threads extending from the opposed leg into the leg extension a distance equal to or less than the length of the leg extension.

3. The bone screw system of claim 2 wherein the wall of each leg or leg extension has a minimum thickness (t) at thread grooves between adjacent threads and the breakaway grooves extends at least to a portion of a thread groove a distance (t) or greater.

4. The bone screw system of claim 3 wherein the internal thread has a pitch and the breakaway groove intersects the pitch.

5. The bone screw system of claim 1 wherein the breakaway groove is oriented perpendicular to a longitudinal axis (AL) of the bone screw system.

6. The bone screw system of claim 1 wherein the enlarged openings are arcuate segments to semicircular in shape.

7. The bone screw system of claim 1 wherein the breakaway groove has a straight upper groove wall and a lower groove wall having a straight inner portion and a chamfered outer portion.

8. The bone screw system of claim 1 wherein the leg attachment of the breakaway groove breaks on movement of the leg extension at a bend angle of 10 degrees or less.

9. The bone screw system of claim 1 wherein the breakaway groove snaps or breaks at less than 10 pounds, but greater than 2 pounds.

10. The bone screw system of claim 1 wherein the breakaway groove snaps or breaks between 3 and 7 pounds.

11. The bone screw system of claim 1 wherein the bone screw system is made of metal.

12. The bone screw system of claim 1 wherein the bone screw system is made of titanium.

13. The bone screw system of claim 1 wherein the opposed leg and leg extensions have an arcuate length, the leg attachments extend along the breakaway groove between the aperture and the undercuts a combined distance less than 75% of the arcuate width of the leg.

14. The bone screw system of claim 1 wherein the breakaway groove is positioned at the coupling location of the opposed legs and each leg extension.

15. A bone screw system comprising:

an elongate fixation element adapted to engage a bone and having a head portion and a threaded shank portion;

a receiving element defining an internal bore sized to receive the shank portion of the fixation element and a seat adapted to support the head portion of the fixation element, the receiving element comprising a pair of opposed legs separated by a rod receiving channel sized for complimentary engagement with a stabilizer rod, wherein the pair of opposed legs defines a compression element receiving chamber, each opposed leg having a wall of a thickness with internal threads extending inwardly from each wall;

a pair of leg extensions, one leg extension coupled to each opposed leg;

a compression element configured to engage a portion of the receiving element and be complimentarily received in the compression element receiving chamber, the compression element configured to compress the stabilizer rod into the receiving element to fix the position of the stabilizer rod with respect to the receiving element, the compression element has external threads complimentary to the internal threads of the opposed legs;

a breakaway groove positioned externally on each leg or leg extension, the breakaway groove extending inwardly at least partially into the wall between each leg and leg extension, wherein the leg or leg extension has a second cut at a leading end of the breakaway groove, the second cut being an undercut to create an enlarged opening and another second cut is positioned at the trailing end of the breakaway groove to create an enlarged opening, the second cuts forming a point of fracture break initiation due to the arcuate shape of the legs, wherein interposed between the undercuts is a leg attachment of the breakaway groove joining the leg to the leg extension, the leg attachment breaks on movement of the leg extension by being bent off a center axis at a bend angle of 10 degrees or less.

16. The bone screw system of claim 15 wherein the enlarged openings are arcuate segments to semicircular in shape.

17. The bone screw system of claim 15 wherein the breakaway groove has a straight upper groove wall and a lower groove wall having a straight inner portion and a chamfered outer portion.

18. The bone screw system of claim 15 wherein the breakaway groove snaps or breaks at less than 10 pounds, but greater than 2 pounds.

19. The bone screw system of claim 18 wherein the breakaway groove snaps or breaks between 3 and 7 pounds.

20. The bone screw system of claim 15 wherein the bone screw system is made of metal.

21. The bone screw system of claim 15 wherein the bone screw system is made of titanium.

22. The bone screw system of claim 15 wherein the opposed leg and leg extensions have an arcuate length, the leg attachment extends along the breakaway groove between the undercuts a combined distance less than 75% of the arcuate width of the leg.

23. The bone screw system of claim 15 wherein the breakaway groove is positioned at the coupling location of the opposed legs and each leg extension.

24. The bone screw system of claim 15 wherein the breakaway groove is oriented perpendicular to a longitudinal axis (AL) of the bone screw system.

* * * * *